(12) United States Patent
Michael et al.

(10) Patent No.: US 11,111,209 B2
(45) Date of Patent: Sep. 7, 2021

(54) PROCESS FOR RECOVERING ACETONITRILE FROM ACRYLONITRILE WASTE STREAMS

(71) Applicant: Ascend Performance Materials Operations LLC, Houston, TX (US)

(72) Inventors: Basil Michael, Houston, TX (US); Carl Alexander Diaz, Pearland, TX (US); Billy Nelson, Alvin, TX (US); Kyle Kissell, Manvel, TX (US)

(73) Assignee: Ascend Performance Materials Operations LLC, Houston, TX (US)

( * ) Notice: Subject to any disclaimer, the term of this patent is extended or adjusted under 35 U.S.C. 154(b) by 0 days.

(21) Appl. No.: 16/682,167

(22) Filed: Nov. 13, 2019

(65) Prior Publication Data

US 2020/0157044 A1 May 21, 2020

Related U.S. Application Data

(60) Provisional application No. 62/760,233, filed on Nov. 13, 2018.

(51) Int. Cl.
*C07C 253/34* (2006.01)

(52) U.S. Cl.
CPC .................. *C07C 253/34* (2013.01)

(58) Field of Classification Search
CPC ........................ C07C 253/34; C07C 255/03
See application file for complete search history.

(56) References Cited

U.S. PATENT DOCUMENTS

| | | | | |
|---|---|---|---|---|
| 4,362,603 A * | 12/1982 | Presson | ................ | C07C 255/00 203/75 |
| 6,204,407 B1 * | 3/2001 | Godbole | ............... | C07C 253/26 558/319 |
| 6,780,289 B2 * | 8/2004 | Godbole | ............... | C07C 253/24 203/79 |
| 2008/0073201 A1 * | 3/2008 | Van Gysel | ............ | C07C 253/34 203/34 |

FOREIGN PATENT DOCUMENTS

| | | | |
|---|---|---|---|
| WO | 2005044783 | | 5/2005 |
| WO | WO 2017/120566 | * | 7/2017 |

OTHER PUBLICATIONS

Zhu et al. (Separation and Purificaton Technology 169 (2016) 66-77)—provided by Applicants.*
Asmaiqbal et al., "Overview of Enhanced Distillations", International Journal of Advance in Science and Engineering, vol. 4, Issue 11, Nov. 2015, pp. 263-270.
International Application No. PCT/US2019/061099, "International Search Report and Written Opinion", dated Feb. 17, 2020, 13 pages.
Zhu et al., "Separation of Acetonitrile/Methanol/Benzene Ternary Azeotrope via Triple Column Pressure-Swing Distillation", Separation and Purification Technology, vol. 169, 2016, pp. 66-77.

* cited by examiner

*Primary Examiner* — Valerie Rodriguez-Garcia
(74) *Attorney, Agent, or Firm* — Cozen O'Connor

(57) ABSTRACT

A process for producing a high-purity acetonitrile product from a low-purity acetonitrile feedstock streams. In particular, the present disclosure relates to a process for producing a sales-grade, high purity acetonitrile by (a) distilling the feedstock stream in a to yield a crude acetonitrile stream, (b) treating the crude acetonitrile stream to produce an intermediate acetonitrile stream, (c) purifying the intermediate acetonitrile stream in a pressure swing distillation system to produce a recycle stream and an acetonitrile product stream, (d) recycling the recycle stream to the first distillation column, and (e) distilling the acetonitrile product stream to yield a purified acetonitrile product stream of at least 98 wt. % acetonitrile.

23 Claims, 3 Drawing Sheets

PROCESS FOR RECOVERING ACETONITRILE FROM ACRYLONITRILE WASTE STREAMS

CROSS-REFERENCE TO RELATED APPLICATIONS

The present application claims priority to and filing benefit of U.S. Provisional Patent Application No. 62/760,233, filed on Nov. 13, 2018, which is incorporated herein by reference in its entirety.

FIELD

The present disclosure relates generally to recovery of acetonitrile from industrial processes. More specifically, the present disclosure relates to process for recovering acetonitrile from acrylonitrile waste streams comprising methanol.

BACKGROUND

Cyanocarbons, e.g., organic compounds having cyano functional groups, are known and are widely used in various applications. Many of these compounds, including acrylonitrile, are used as monomers to prepare various polymers, such as nylon, polyacrylonitrile, or acrylonitrile butadiene styrene. Several methods of producing cyanocarbons are known in the art, and these production methods often yield waste streams comprising small amounts of desirable coproducts. For example, acetonitrile may be present in many of the conventional waste streams of industrial acrylonitrile production processes. Typically, this co-product acetonitrile may be recovered using well-known separation schemes. These typical acrylonitrile process waste stream separation schemes, however, do not contemplate the presence of some impurities in the waste streams, e.g., methanol, which can be precarious due to its ability to azeotrope with acetonitrile.

A number of processes for recovering acetonitrile are known in the art. For example, U.S. Pat. No. 4,362,603 discloses a process for recovering an acetonitrile byproduct from a stream comprising acetonitrile, water, HCN, acrylonitrile, and other organics such as oxazole, allyl alcohol, acetone, or propionitrile by distilling in three distillation zones at varying pressures.

As another example, U.S. Pat. No. 6,780,289 discloses a method for the purification of crude acetonitrile comprising distilling the crude acetonitrile in a first fractional distillation column at below atmospheric pressure, withdrawing a first side draw fraction comprising acetonitrile, the first side draw fraction in a second fractional distillation column at super atmospheric pressure, and withdrawing from the second distillation a second side draw fraction comprising purified acetonitrile.

While these references may relate to acetonitrile separation, these references fail to contemplate unique feedstock streams that comprise methanol and/or the challenges of separations involving propionitrile. Thus, the need exists for improved processes that effectively separate and/or recover by-product acetonitrile from methanol-containing acrylonitrile production process waste streams.

SUMMARY

In some aspects, the present disclosure relate to a process for recovering acetonitrile, comprising the steps of distilling a feedstock stream comprising methanol and acetonitrile in a first distillation column to yield a crude acetonitrile stream, treating the crude acetonitrile stream to remove hydrogen cyanide and produce an intermediate acetonitrile stream comprising less than 1 wt. % hydrogen cyanide, purifying the intermediate acetonitrile stream in a pressure swing distillation system to produce an acetonitrile product stream and a recycle stream, purifying the acetonitrile product stream to form a purified acetonitrile product stream comprising at least 98 wt. % acetonitrile. In some aspects, the pressure swing distillation system comprises: a low pressure distillation column and a high pressure distillation column and wherein the high pressure distillation column yields an overhead stream and a bottoms stream. In some aspects, the recycle stream is the overhead stream of the high pressure distillation column. In some aspects, the acetonitrile product stream is the bottoms stream of the high pressure distillation column. The process wherein the low pressure distillation column operates at a pressure less than −5 psig. In some aspects, the high pressure distillation column operates at a pressure greater than 10 psig. In some aspects, the acetonitrile product stream comprises less than 1 wt. % methanol, the feedstock stream further comprises oxazole and propionitrile, the intermediate acetonitrile stream comprises less than 0.01 wt. % hydrogen cyanide, and the purified acetonitrile product stream comprises at least 99.5 wt. % acetonitrile. In some aspects, the process further comprises the step of recycling the recycle stream, which comprises methanol, to the first distillation column. In some aspects, the recycle stream comprises at least 0.01 wt. % methanol. In some aspects, the recycle stream comprises from 0.01 wt. % to 5 wt. % methanol. In some aspects, the purifying of the acetonitrile product stream comprises distilling the acetonitrile product stream to yield the purified acetonitrile product stream. In some aspects, the feedstock stream comprises at least 0.05 wt. % methanol In some aspects, the feedstock stream comprises less than 5 wt. % acetonitrile. In some aspects, the feedstock stream further comprises propionitrile. In some aspects, the treating comprises reacting the crude acetonitrile stream with a caustic solution to react out hydrogen cyanide. In some aspects, the crude acetonitrile stream comprises from 0.1 wt. % to 5 wt. % hydrogen cyanide. In some aspects, the intermediate acetonitrile stream comprises less than 0.05 wt. % hydrogen cyanide. In some aspects, the feedstock stream comprises one or more waste streams from acrylonitrile production processes. In some aspects, the purified acetonitrile product stream comprises at least 99.9 wt. % acetonitrile. In some aspects, the purified acetonitrile product stream comprises less than 0.1 wt. % of propionitrile.

In some aspects, the present disclosure describes a process for recovering acetonitrile, comprising the steps of distilling a feedstock stream comprising methanol and acetonitrile in a first distillation column to yield a crude acetonitrile stream, treating the crude acetonitrile stream to remove hydrogen cyanide and produce an intermediate acetonitrile stream comprising less than 1 wt. % hydrogen cyanide, and purifying the intermediate acetonitrile stream in a pressure swing distillation system to produce a recycle stream and an acetonitrile product stream comprising at least 90 wt. % acetonitrile.

BRIEF DESCRIPTION OF THE DRAWINGS

The present disclosure is described in detail below with reference to the appended drawings, wherein like numerals designate similar parts.

DETAILED DESCRIPTION

Figure 1:
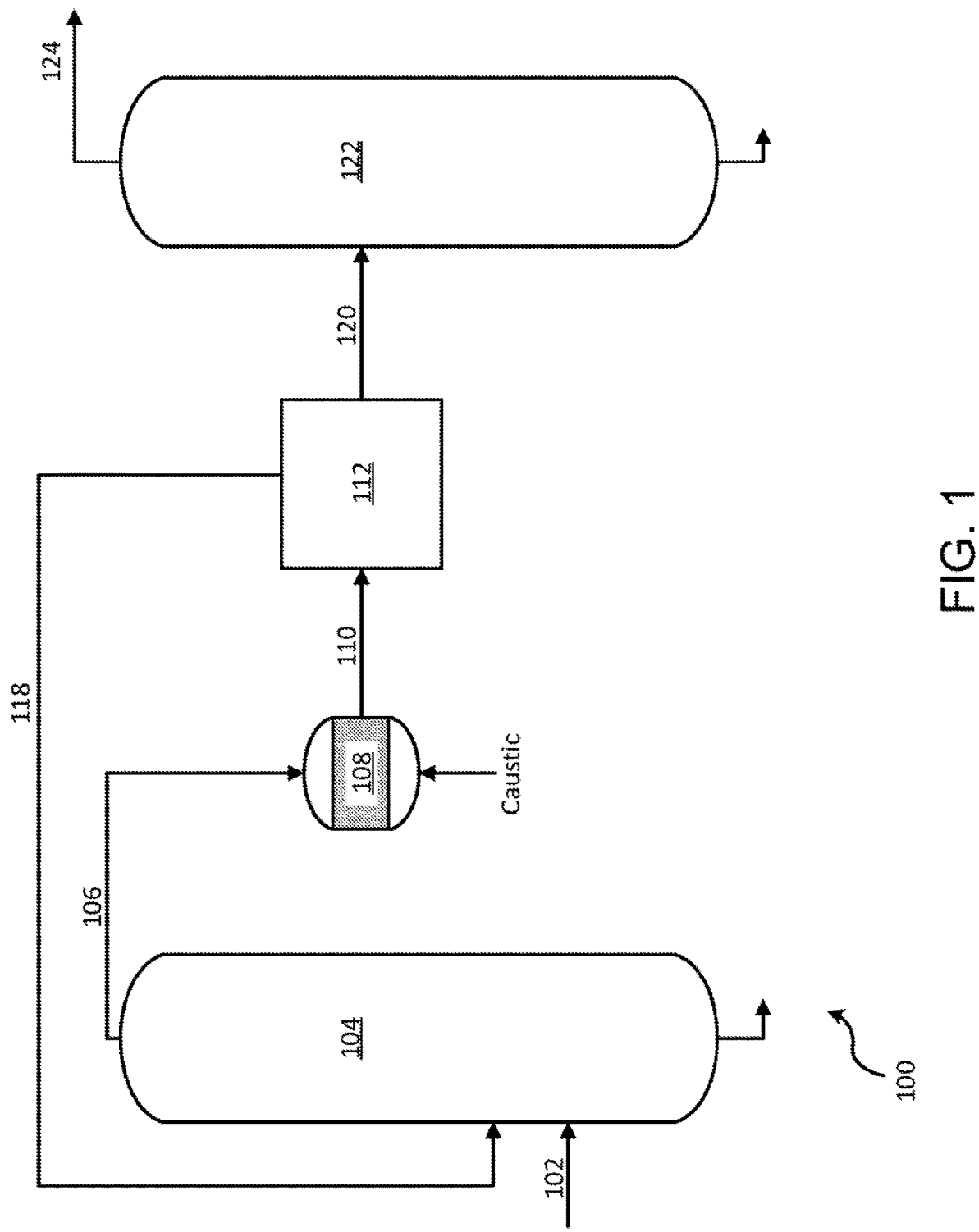
FIG. 1 illustrates a schematic of a process for recovering acetonitrile in accordance with embodiments of the disclosure.

As noted above, conventional acrylonitrile production process waste streams contain amounts of desirable co-products, e.g., acetonitrile, which may be recovered and/or purified to yield saleable (acetonitrile) product. The inventors have found that, in some cases, the acetonitrile-containing waste streams may comprise other impurities, e.g., methanol, which were not previously contemplated in separation schemes. In some cases, it has been discovered that methanol may be employed in acrylonitrile reactors to favor the production of hydrogen cyanide, which, in turn, may contribute to process efficiencies. This methanol may then carry through to the remainder of the production process and ultimately be present in the acrylonitrile waste streams. Methanol, regardless of the source and even in small amounts, has been found to create significant problems in the separation and/or purification of the by-product acetonitrile. As one example, it has been found that methanol has the ability to detrimentally azeotrope with the by-product acetonitrile, thus resulting in separation inefficiencies, poor final purity levels, and low yields. Conventional acetonitrile recovery processes provide little or no guidance relating to effective separation of feedstock streams that comprise methanol.

It has also been found that the acetonitrile-containing waste streams may comprise further impurities, e.g., propionitrile. Propionitrile may be present as an additional co-product of conventional acrylonitrile production processes and has also been found to create significant problems in the separation and/or purification of the by-product acetonitrile. Conventional methods of separation and/or purification of the co-product acetonitrile provide little or no guidance relating to effective propionitrile separation. As a result, the propionitrile may remain present in the final product of these conventional methods, resulting in poor final purity levels and low yields.

The inventors have now found that the separation of particular waste streams, e.g., methanol-containing and/or propionitrile-containing acrylonitrile production process waste streams, using a specific separation scheme (disclosed herein) advantageously results in significant quantities of high purity acetonitrile product. Without being bound by theory, it is believed that the use of, inter alia, a pressure swing distillation system, prior to final acetonitrile purification, beneficially, prevents methanol build-up in the downstream separation units. This reduction or elimination of methanol, in turn, leads to a reduction or elimination of methanol-acetonitrile azeotrope, which advantageously reduces the need for complex separation processes to break the azeotrope and further separate the components. Further, the inventors have discovered that the aforementioned methanol removal contributes to unexpected efficiencies in (downstream) propionitrile separation, e.g., in a column configured downstream of the pressure swing distillation system.

The present disclosure relates to a process for producing a high-purity acetonitrile product from a low-purity acetonitrile feedstock that contains methanol. The process comprises the step of distilling a feedstock stream comprising methanol and low amounts of acetonitrile, e.g., less than 5 wt. %, in a first distillation column to yield a crude acetonitrile stream. The process further comprises the step of treating the crude acetonitrile stream to remove hydrogen cyanide therefrom, thus producing an intermediate acetonitrile stream low amounts of hydrogen cyanide, e.g., less than 1 wt. % hydrogen cyanide. The low hydrogen cyanide content intermediate acetonitrile stream is purified (separated) in one or more distillation columns to produce an acetonitrile product stream and a recycle stream. In some cases, this purification is performed in a pressure swing distillation system. The process further comprises the step of purifying the acetonitrile product stream, optionally in a fourth column, to form a purified acetonitrile product stream, e.g., comprising at least 95 wt. % acetonitrile, e.g., at least 97 wt. %, at least 98 wt. %, at least 99 wt. %, at least 99.9 wt. %, or at least 99.99 wt. %. Conventional separation processes have been found to be unable to achieve such high levels of acetonitrile purity.

Feedstock

As noted above, the presence of methanol in the feedstock has been found to create significant separation issues and to limit the ability to recover a highly pure acetonitrile product. For instance, methanol has been found to form an azeotrope with the desired acetonitrile.

The process of the present disclosure may begin with a specific methanol-containing and/or propionitrile-containing feedstock stream, which, as noted above, has been found to create multiple, significant separation issues. In some cases, oxazole may also be present, and the oxazole may further complicate separation, due to its chemical structure and physical properties. The feedstock comprises (low amounts of) acetonitrile and methanol, as well as optional components such as hydrogen cyanide, acrylonitrile, and (significant amounts) water. In some embodiments, the feedstock stream may be one or more waste streams of another industrial chemical production processes, e.g., the production of acrylonitrile, allyl cyanide, butyronitrile, polyacrylonitrile, polyamides, polyaramids, or combinations thereof. For example, the feedstock stream may comprise one or more waste streams from such processes. In a specific case, the feedstock stream may be one or more waste streams, e.g., purge streams, from an acrylonitrile production process. For example, waste streams from multiple processes for producing organic nitriles or derivatives thereof may be combined to form the feedstock stream.

In conventional processes, acetonitrile-containing waste streams of acrylonitrile production processes are burned in waste heat boilers to suppress the formation of nitrogen oxides. This solution, however, fails to capture the by-product acetonitrile. In the processes of the present disclosure, however, these waste streams may be processed to recover the acetonitrile, preferably in at a high purity level.

The feedstock stream of the present disclosure comprises acetonitrile. In some embodiments, the feedstock stream comprises a relatively low content of acetonitrile. In one embodiment, the feedstock comprises acetonitrile in an amount ranging from 0.05 wt. % to 10.0 wt. %, based on the total weight of the feedstock stream, e.g., from 0.05 wt. % to 7.0 wt. %, from 0.1 wt. % to 5.0 wt. %, from 0.1 wt. % to 7.0 wt. %, from 0.5 wt. % to 5.0 wt. %, from 0.5 wt. % to 4.0 wt. %, from 1.0 wt. % to 4.0 wt. %, or from 1.0 wt. % to 3.0 wt. %. In terms of upper limits, the feedstock stream may comprise less than 10.0 wt. % acetonitrile, e.g., less than 7.0 wt. %, less than 5.0 wt. %, less than 4.0 wt. %, or less than 3.0 wt. %. In terms of lower limits, the feedstock stream may comprise greater than 0.05 wt. % acetonitrile, e.g., greater than 0.1 wt. %, greater than 0.5 wt. %, or greater than 1.0 wt. %.

Generally, as used herein, the weight percentages are based on the total weight of the respective stream. With respect to the feedstock, the weight percentages include all components of the feedstock, including a significant portion of water. In some embodiments, for example, the feedstock comprises at least 50 wt. % water, e.g., at least 60 wt. %, at least 70 wt. %, at least 75 wt. %, or at least 80 wt. %. It is contemplated that a feed stream comprising less water, e.g., a partially dehydrated or fully dehydrated feed stream, may be employed. In such a case, the component percentages discussed herein could easily be recalculated/derived by starting with the aforementioned component percentages and recalculating based on a lesser amount of water, e.g., taking water out of the basis for the weight percent calculation.

The feedstock stream also comprises methanol. In one embodiment, the feedstock comprises methanol in an amount ranging from 0.01 wt. % to 1 wt. %, e.g., from 0.01 wt. % to 0.5 wt. %, from 0.01 wt. % to 0.3 wt. %, from 0.05 wt. % to 1 wt. %, from 0.05 wt. % to 0.5 wt. %, from 0.05 wt. % to 0.3 wt. %, from 0.075 wt. % to 1 wt. %, from 0.075 wt. % to 0.5 wt. %, or from 0.075 wt. % to 0.3 wt. %. In terms of upper limits, the feedstock stream may comprise less than 1 wt. % methanol, e.g., less than 0.5 wt. %, or less than 0.3 wt. %. In terms of lower limits, the feedstock stream may comprise greater than 0.01 wt. % methanol, e.g., greater than 0.05 wt. %, or greater than 0.075 wt. %.

The feedstock stream may further comprise propionitrile. In one embodiment, the feedstock comprises propionitrile in an amount ranging from 0.01 wt. % to 1 wt. %, e.g., from 0.01 wt. % to 0.5 wt. %, from 0.01 wt. % to 0.3 wt. %, from 0.05 wt. % to 1 wt. %, from 0.05 wt. % to 0.5 wt. %, from 0.05 wt. % to 0.3 wt. %, from 0.075 wt. % to 1 wt. %, from 0.075 wt. % to 0.5 wt. %, or from 0.075 wt. % to 0.3 wt. %. In terms of upper limits, the feedstock stream may comprise less than 1 wt. % propionitrile, e.g., less than 0.5 wt. %, or less than 0.3 wt. %. In terms of lower limits, the feedstock stream may comprise greater than 0.01 wt. % propionitrile, e.g., greater than 0.05 wt. %, or greater than 0.075 wt. %.

The feedstock stream may also comprise oxazole. In one embodiment, the feedstock comprises oxazole in an amount ranging from 0.01 wt. % to 1 wt. %, e.g., from 0.01 wt. % to 0.5 wt. %, from 0.01 wt. % to 0.3 wt. %, from 0.01 wt. % to 0.1 wt. %, from 0.05 wt. % to 1 wt. %, from 0.05 wt. % to 0.5 wt. %, from 0.05 wt. % to 0.3 wt. %, from 0.05 wt. % to 0.1 wt. %, from 0.075 wt. % to 1 wt. %, from 0.075 wt. % to 0.5 wt. %, from 0.075 wt. % to 0.3 wt. %, or 0.075 wt. % to 0.1 wt. %. In terms of upper limits, the feedstock stream may comprise less than 1 wt. % oxazole, e.g., less than 0.5 wt. %, less than 0.3 wt. %, or less than 0.1 wt. %. In terms of lower limits, the feedstock stream may comprise greater than 0.01 wt. % oxazole, e.g., greater than 0.05 wt. %, or greater than 0.075 wt. %.

In some embodiments, the feedstock stream also comprises hydrogen cyanide. In one embodiment, the feedstock comprises hydrogen cyanide in an amount ranging from 0.01 wt. % to 2 wt. %, e.g., from 0.01 wt. % to 1 wt. %, from 0.01 wt. % to 0.5 wt. %, from 0.01 wt. % to 0.3 wt. %, from 0.05 wt. % to 2 wt. %, from 0.05 wt. % to 1 wt. %, from 0.05 wt. % to 0.5 wt. %, from 0.05, to 0.3 wt. %, from 0.075 wt. % to 2 wt. %, from 0.075 wt. % to 1 wt. %, from 0.075 to 0.5 wt. %, from 0.075 wt. % to 0.3 wt. % from 0.1 wt. % to 2 wt. %, from 0.1 wt. % to 1 wt. %, from 0.1 wt. % to 0.5 wt. %, or from 0.1 wt. % to 0.5 wt. %. In terms of upper limits, the feedstock stream may comprise less than 2 wt. %, e.g., less than 1 wt. %, less than 0.5 wt. %, or less than 0.3 wt. %. In terms of lower limits, the feedstock stream may comprise greater than 0.01 wt. %, e.g., greater than 0.05 wt. %, greater than 0.075 wt. %, or greater than 0.1 wt. %.

The feedstock stream of the present disclosure may also comprise various impurities, typically in small amounts, e.g., ppm or ppb. These impurities may include various waste products that result from the production of organic nitriles and derivatives thereof. For example, the feedstock stream may comprise acrylamides, azoles, aliphatic nitriles, aromatic nitriles, alcohols, aldehydes, acrolein, fumarin, acrylamide, and cyanide salts.

First Distillation

As noted above, the feedstock stream is distilled in a first distillation column to yield a crude acetonitrile stream. The first distillation, in some cases, removes a significant portion (if not all) of the hydrogen cyanide present in the feedstock stream. The inventors have found that the removal of hydrogen cyanide prior to processing in additional separation units, e.g., columns, takes advantage of the low boiling point of hydrogen cyanide, which in turn provides for separation efficiency improvements downstream, e.g., reduction or elimination of separate hydrogen cyanide separation units.

The structure of the first distillation column may vary widely. And various distillation columns are known to those of ordinary skill in the art, and any suitable column may be employed as long as the aforementioned separation is achieved. For example the first distillation column may comprise any suitable separation device or combination of separation devices. For example, the first distillation column may comprise a column, e.g., a standard distillation column, an extractive distillation column and/or an azeotropic distillation column. In some cases, the term "first distillation column" may refer to multiple distillation columns configured with one another.

In some embodiments, the first distillation column operates at a pressure ranging from 0 psig to 10 psig, e.g., from 0 psig to 9 psig, from 0 psig to 8 psig, from 0 psig to 7 psig, from 0 psig to 6 psig, from 0.5 psig to 10 psig, from 0.5 psig to 9 psig, from 0.5 psig to 8 psig, from 0.5 psig to 7 psig, from 0.5 psig to 6 psig, from 1 psig to 10 psig, from 1 psig to 9 psig, from 1 psig to 8 psig, from 1 psig to 7 psig, from 1 psig to 6 psig, from 1.5 psig to 10 psig, from 1.5 psig to 9 psig, from 1.5 psig to 8 psig, from 1.5 psig to 7 psig, from 1.5 psig to 6 psig, from 2 psig to 10 psig, from 2 psig to 9 psig, from 2 psig to 8 psig, from 2 psig to 7 psig, or from 2 psig to 6 psig. In terms of lower limits, the first distillation column may operate at a pressure greater than 0 psig, e.g., greater than 0.5 psig, greater than 1 psig, greater than 1.5 psig, or greater than 2 psig. In terms of upper limits, the first distillation column may operate at a pressure less than 10 psig, e.g., less than 9 psig, less than 8 psig, less than 7 psig, or less than 6 psig.

In some embodiments, the first distillation column operates at a temperature ranging from 125° F. to 275° F., e.g., from 125° F. to 260° F., from 125° F. to 250° F., from 125° F. to 240° F., from 130° F. to 275° F., from 130° F. to 260° F., from 130° F. to 250° F., from 130° F. to 240° F., from 140° F. to 275° F., from 140° F. to 260° F., from 140° F. to 250° F., from 140° F. to 240° F., from 150° F. to 275° F., from 150° F. to 260° F., from 150° F. to 250° F., or from 150° F. to 240° F. In terms of lower limits, the first distillation column may operate a temperature greater than 125° F., e.g., greater than 130° F., greater than 140° F., or greater than 150° F. In terms of upper limits, the first distillation column may operate a temperature less than 275° F., e.g., less than 260° F., less than 250° F., or less than 240° F.

HCN Treatment

As noted above, the feedstock may comprise various impurities, including hydrogen cyanide. Some of these impurities may remain present in the crude acetonitrile stream after the distillation in the first distillation column. In order to remove some of these impurities, particularly hydrogen cyanide, the process comprises the step of treating the crude acetonitrile stream to remove, inter alia, hydrogen cyanide. The treating step yields the intermediate acetonitrile stream, which contains little or no hydrogen cyanide.

In some embodiments, treatment of the crude acetonitrile stream comprises reacting the crude acetonitrile stream with a caustic solution, which may react with the hydrogen cyanide, thus consuming hydrogen cyanide in the crude acetonitrile stream. The caustic solution may vary widely. For example the caustic solution may comprise a strong base, especially alkali bases. For example, the caustic solution may comprise sodium hydroxide, potassium hydroxide, magnesium hydroxide, calcium hydroxide, or combinations thereof. In preferred embodiments, the caustic solution is a solution of sodium hydroxide. The caustic solution may also comprise other compounds. For example, the caustic solution may comprise an aldehyde, such as formaldehyde.

In some embodiments, treatment of the crude acetonitrile stream occurs in a digester, which may be heated to increase the rate of the treatment reaction. In some embodiments, the digester of the treatment step is operated at a temperature greater than 150° F., e.g., greater than 160° F., greater than 170° F., or greater than 180° F. In terms of upper limits, the digester may be operated at a temperature less than 300° F., e.g., less than 290° F., less than 280° F., or less than 275° F. In terms of ranges, the digester may be operated at a temperature from 150° F. to 300° F., e.g., from 150° F. to 290° F., from 150° F. to 280° F., from 150° F. to 275° F., from 160° F. to 300° F., from 160° F. to 290° F., from 160° F. to 280° F., from 160° F. to 275° F., from 170° F. to 300° F., from 170° F. to 290° F., from 170° F. to 280° F., from 170° F. to 275° F., from 180° F. to 300° F., from 180° F. to 290° F., from 180° F. to 280° F., or from 180° F. to 275° F.

In one embodiment, the crude acetonitrile stream comprises hydrogen cyanide in an amount ranging from 0.01 wt. % to 10 wt. %, e.g., from 0.01 wt. % to 5 wt. %, from 0.01 to 2 wt. %, from 0.1 wt. % to 10 wt. %, from 0.1 wt. % to 5 wt. %, from 0.1 wt. % to 2 wt. %, from 0.5 wt. % to 10 wt. %, from 0.5 wt. % to 5 wt. %, from 0.5 wt. % to 2 wt. %, from 1 wt. % to 10 wt. %, from 1 wt. % to 5 wt. %, or from 1 wt. % to 2 wt. %. In terms of upper limits, the crude acetonitrile stream may comprise less than 10 wt. % of hydrogen cyanide, e.g., less than 5 wt. %, or less than 2 wt. %. In terms of lower limit, the crude acetonitrile stream may comprise greater than 0.01 wt. % hydrogen cyanide, e.g., greater than 0.1 wt. %, greater than 0.5 wt. %, and greater than 1 wt. %.

By treating the crude acetonitrile stream, some or all of the (remaining) hydrogen cyanide impurity in the stream may be consumed. In one embodiment, the entirety of the hydrogen cyanide content of the crude acetonitrile stream may be consumed. In some embodiments, the resulting intermediate acetonitrile stream may comprise a relatively low amount of hydrogen cyanide. In one embodiment, the intermediate acetonitrile stream comprises hydrogen cyanide in an amount ranging from 0 wt. % to 0.1 wt. %, e.g., from 0 wt. % to 0.05 wt. %, from 0 wt. % to 0.01 wt. %, from 0 wt. % to 0.005 wt. %, from 0 wt. % to 0.001 wt. %, from 0.0001 wt. % to 0.1 wt. %, from 0.0001 wt. % to 0.05 wt. %, from 0.0001 wt. % to 0.01 wt. %, from 0.0001 wt. % to 0.005 wt. %, from 0.0001 wt. % to 0.001 wt. %, from 0.00005 wt. % to 0.1 wt. %, from 0.00005 wt. % to 0.05 wt. %, from 0.00005 wt. % to 0.01 wt. %, from 0.00005 wt. % to 0.005 wt. %, from 0.00005 wt. % to 0.001 wt. %. In terms of upper limits, the intermediate acetonitrile stream may comprise less than 0.1 wt. % hydrogen cyanide, e.g., less than 0.05 wt. %, less than 0.01 wt. %, less than 0.005 wt. %, and less than 0.001 wt. %. In terms of lower limits, the intermediate acetonitrile stream may comprise greater than 0 wt. % hydrogen cyanide, e.g., greater than 0.00005 wt. %, or greater than 0.0001 wt. %.

The intermediate acetonitrile stream comprises other impurities, such as oxazole, that must be removed. In one embodiment, the intermediate acetonitrile stream comprises oxazole in an amount ranging from 0.1 wt. % to 5 wt. %, e.g., from 0.1 wt. % to 4 wt. %, from 0.1 wt. % to 3 wt. %, from 0.1 wt. % to 2 wt. %, from 0.2 wt. % to 5 wt. %, from 0.2 wt. % to 4 wt. %, from 0.2 wt. % to 3 wt. %, from 0.2 wt. % to 2 wt. % from 0.5 wt. % to 5 wt. %, from 0.5 wt. % to 4 wt. %, from 0.5 wt. % to 3 wt. %, from 0.5 wt. % to 2 wt. %, from 1 wt. % to 5 wt. %, from 1 wt. % to 4 wt. %, from 1 wt. % to 3 wt. %, or from 1 wt. % to 2 wt. %. In terms of upper limits, the intermediate acetonitrile stream may comprise less than 5 wt. % oxazole, e.g., less than 4 wt. %, less than 3 wt. %, or less than 2 wt. %. In terms of lower limits, the intermediate acetonitrile stream may comprise greater than 0.1 wt. %, e.g., greater than 0.2 wt. %, greater than 0.5 wt. %, or greater than 1 wt. %.

In some cases, the first distillation and the hydrogen cyanide treatment may be combined into a single system. In such a case the stream exiting the combined first distillation/hydrogen cyanide removal may comprise little or no hydrogen cyanide. And this exiting stream may be similar in composition to the intermediate acetonitrile stream.

Pressure Swing Distillation

Treatment of the crude acetonitrile stream produces an intermediate acetonitrile stream. As noted above, the intermediate acetonitrile stream is purified in a pressure swing distillation system to produce an acetonitrile product stream. The pressure swing distillation system utilizes the effect of pressure on evaporation and distillation to purify the intermediate acetonitrile stream. In some embodiments, the pressure swing distillation system may comprise a series of distillation columns that operate at varying pressures, e.g., a low pressure distillation column and a high pressure distillation column. For example, the pressure swing distillation system may first distill the intermediate acetonitrile stream in a low pressure distillation column and then a high pressure distillation column; alternatively, the pressure swing distillation system may first distill the intermediate acetonitrile stream in a high pressure distillation column and then a low pressure distillation column. In some embodiments, the pressure swing distillation system may comprise a greater number of distillation columns, e.g., a low pressure distillation column, a middle pressure distillation column, and a high pressure distillation column. In other embodiments, the pressure swing distillation system may comprise one or more columns wherein the pressure within a given column is manipulated, e.g., by a pump. For example, the pressure first distill the intermediate acetonitrile stream in a pressure-controlled distillation column at a low pressure and then increase the pressure in the pressure-controlled distillation column to distill the intermediate acetonitrile stream at a high pressure.

The pressure swing distillation system, regardless of the structure, operates by distilling the intermediate acetonitrile stream at varying pressures. In some embodiments, the pressure swing distillation system comprises a low pressure second column and a high pressure third column. And the combination of the distillations at varying pressures unexpectedly provides for improvements in overall separation of the components, e.g., the acetonitrile and/or the methanol and/or the acetonitrile-methanol azeotrope.

In some embodiments, the low pressure column of the pressure swing distillation system, e.g., a low pressure second column, operates at a pressure ranging from less than −15 psig to 0 psig, e.g., from −10 psig to 0 psig, from −8 psig to 0 psig, from −5 psig to 0 psig, from −15 psig to −1 psig, from −10 psig to −1 psig, from −8 psig to −1 psig, from −5 psig to −1 psig, from −15 psig to −2 psig, from −10 psig to −2 psig, from −8 psig to −2 psig, or from −5 psig to −2 psig. In terms of upper limits, the low pressure second column may operate at a pressure less than 0 psig, e.g., less than −1 psig, or less than −2 psig. In terms of lower limits, the low pressure second column may operate at a pressure greater than −15 psig, e.g., greater than −10 psig, greater than −8 psig, or greater than −5 psig.

In some embodiments, the high pressure column of the pressure swing distillation system, e.g., a high pressure third column, operates at a pressure ranging from 10 psig to 50 psig, e.g., from 15 psig to 50 psig, from 25 psig to 50 psig, from 30 psig to 50 psig, from 10 psig to 45 psig, from 15 psig to 45 psig, from 25 psig to 45 psig, from 30 psig to 45 psig, from 10 psig to 40 psig, from 15 psig to 40 psig, from 25 psig to 40 psig, or from 30 psig to 40 psig. In terms of upper limits, the high pressure third column may operate at a pressure less than 50 psig, e.g., less than 45 psig, or less than 40 psig. In terms of lower limits, the high pressure third column may operate at a pressure greater than 10 psig, e.g., greater than 15 psig, greater than 25 psig, or greater than 30 psig.

In some embodiments, the high pressure third column operates at a temperature ranging from 225° F. to 325° F., e.g., from 225° F. to 320° F., from 225° F. to 310° F., from 225° F. to 300° F., from 230° F. to 325° F., from 230° F. to 320° F., from 230° F. to 310° F., from 230° F. to 300° F., from 240° F. to 325° F., from 240° F. to 320° F., from 240° F. to 310° F., from 240° F. to 300° F., from 250° F. to 325° F., from 250° F. to 320° F., from 250° F. to 310° F., or from 250° F. to 300° F. In terms of lower limits, the high pressure third column may operate a temperature greater than 225° F., e.g., greater than 230° F., greater than 240° F., or greater than 250° F. In terms of upper limits, the high pressure third column may operate a temperature less than 325° F., e.g., less than 320° F., less than 310° F., or less than 300° F.

Within the pressure swing distillation system, the acetonitrile may form an acetonitrile-water azeotrope. In one embodiment, the pressure swing distillation system comprises the acetonitrile-water azeotrope in an amount ranging from 75 wt. % to 100 wt. %, e.g., from 75 wt. % to 99.9 wt. %, from 75 wt. % to 99 wt. %, from 75 wt. % to 98 wt. %, from 75 wt. % to 97 wt. %, from 80 wt. % to 100 wt. %, from 80 wt. % to 99.9 wt. %, from 80 wt. % to 99 wt. %, from 80 wt. % to 98 wt. %, from 80 wt. % to 97 wt. %, from 85 wt. % to 100 wt. %, from 85 wt. % to 99.9 wt. %, from 85 wt. % to 99 wt. %, from 85 wt. % to 98 wt. %, from 85 wt. % to 97 wt. %, from 90 wt. % to 100 wt. %, from 90 wt. % to 99.9 wt. %, from 90 wt. % to 99 wt. %, from 90 wt. % to 98 wt. %, from 90 wt. % to 97 wt. %, from 95 wt. % to 100 wt. %, from 95 wt. % to 99.9 wt. %, from 95 wt. % to 99 wt. %, from 95 wt. % to 98 wt. %, or from 95 wt. % to 97 wt. %. In terms of upper limits, the pressure swing distillation unit may comprise less than 100 wt. % acetonitrile-water azeotrope, e.g., less than 99.9 wt. %, less than 99 wt. %, less than 98 wt. %, or less than 97 wt. %. In terms of lower limits, the pressure swing distillation unit may comprise greater than 75 wt. % acetonitrile-water azeotrope, e.g., greater than 80 wt. %, greater than 85 wt. %, or greater than 90 wt. %, or greater than 95 wt. %.

Stated another way, within the pressure swing distillation system, acetonitrile may be present in an azeotroped form, e.g., as a portion of an azeotrope. In one embodiment, the pressure swing distillation system comprises azeotroped acetonitrile in an amount ranging from 65 wt. % to 90 wt. %, e.g., from 65 wt. % to 89 wt. %, from 65 wt. % to 88 wt. %, from 65 wt. % to 87 wt. %, from 70 wt. % to 90 wt. %, from 70 wt. % to 89 wt. %, from 70 wt. % to 88 wt. %, from 70 wt. % to 87 wt. %, from 75 wt. % to 90 wt. %, from 75 wt. % to 89 wt. %, from 75 wt. % to 88 wt. %, from 75 wt. % to 87 wt. %, from 80 wt. % to 90 wt. %, from 80 wt. % to 89 wt. %, from 80 wt. % to 88 wt. %, from 80 wt. % to 87 wt. %, from 85 wt. % to 90 wt. %, from 85 wt. % to 89 wt. %, from 85 wt. % to 88 wt. %, or from 85 wt. % to 87 wt. %. In terms of upper limits, the pressure swing distillation unit may comprise less than 90 wt. % azeotroped acetonitrile, e.g., less than 89 wt. %, less than 88 wt. %, or less than 87 wt. %. In terms of lower limits, the pressure swing distillation unit may comprise greater than 65 wt. % azeotroped acetonitrile, e.g., greater than 70 wt. %, greater than 75 wt. %, greater than 80 wt. %, or greater than 85 wt. %. Distillation at varying pressures unexpectedly provides for improvements in separating the azeotroped acetonitrile from the azeotrope.

The pressure swing distillation, generally, yields an overhead stream and a bottoms stream. In some cases, the high pressure distillation column of the pressure swing distillation system yields the overhead stream and the bottoms stream. The overhead stream comprises methanol, e.g., some or all of the methanol that may remain in the intermediate acetonitrile stream after treatment. The overhead stream, e.g., the recycle stream, may advantageously be recycled to the first distillation column to further separate methanol therefrom. In doing so, this methanol is prevented from being conveyed downstream of the pressure swing distillation system, e.g., to the fourth column, which beneficially improves the final purification of the bottoms stream, e.g., the acetonitrile product stream. Because the pressure swing distillation system yields a low methanol content bottoms stream, which may be conveyed to the fourth column for acetonitrile purification, the problems associated with methanol and acetonitrile-methanol azeotrope separation, especially in the fourth distillation column, are advantageously mitigated.

In some embodiments, the recycle stream comprises an overhead stream of the pressure swing distillation system. In one embodiment, the recycle stream comprises methanol in an amount ranging from 0.1 wt. % to 10 wt. %, e.g., from 0.1 wt. % to 5 wt. %, from 0.1 wt. % to 3 wt. %, from 0.5 wt. % to 10 wt. %, from 0.5 wt. % to 5 wt. %, from 0.5 wt. % to 3 wt. %, from 0.075 wt. % to 10 wt. %, from 0.75 wt. % to 5 wt. %, or from 0.75 wt. % to 3 wt. %. In terms of upper limits, the recycle stream may comprise less than 10 wt. % methanol, e.g., less than 5 wt. %, or less than 3 wt. %. In terms of lower limits, the recycle stream may comprise greater than 0.1 wt. % methanol, e.g., greater than 0.5 wt. %, or greater than 0.75 wt. %. In one embodiment, the recycle stream comprises acetonitrile in an amount ranging from 20 wt. % to 90 wt. %, e.g., from 20 wt. % to 85 wt. %, from 20 wt. % to 80 wt. %, from 40 wt. % to 90 wt. %, from 40 wt. % to 85 wt. %, from 40 wt. % to 80 wt. %, from 50 wt. % to 90 wt. %, from 50 wt. % to 85 wt. %, or from 50 wt. % to 80 wt. %. In terms of upper limits, the recycle stream may comprise less than 90 wt. % acetonitrile, e.g., less than 85 wt. %, or less than 80 wt. %. In terms of lower limits, the recycle stream may comprise greater than 20 wt. % acetonitrile, e.g., greater than 40 wt. %, or greater than 50 wt. %.

In one embodiment, the bottoms stream, e.g., the acetonitrile product stream, comprises acetonitrile in an amount ranging from 85 wt. % to 100 wt. %, e.g., from 85 wt. % to 99.9 wt. %, from 85 wt. % to 99.5 wt. %, from 87 wt. % to 100 wt. %, from 87 wt. % to 99.9 wt. %, from 87 wt. % to 99.5 wt. %, from 90 wt. % to 100 wt. %, from 90 wt. % to 99.9 wt. %, from 90 wt. % to 99.5 wt. %, from 92 wt. % to 100 wt. %, from 92 wt. % to 99.5 wt. %, from 92 wt. % to 95 wt. %, from 95 wt. % to 100 wt. %, from 95 wt. % to 99.9 wt. %, or from 95 wt. % to 99.5 wt. %. In terms of upper limits, the acetonitrile stream may comprise less than 100 wt. % acetonitrile, e.g., less than 99.9 wt. % or less than 99.5. In terms of lower limits, the purified acetonitrile stream may comprise greater than 85 wt. % acetonitrile, e.g., greater than 87 wt. %, greater than 90 wt. %, greater than 92 wt. %, greater than 95 wt. %, or greater than 97 wt. %.

In one embodiment, the bottoms stream, e.g., the acetonitrile product stream, comprises methanol in an amount ranging from 0 wt. % to 0.5 wt. %, e.g., from 0 wt. % to 0.1 wt. %, from 0 wt. % to 0.05 wt. %, from 0 wt. % to 0.01 wt. %, from 0 wt. % to 0.005 wt. %, from 0 wt. % to 0.0001 wt. %, from 0.00005 wt. % to 0.5 wt. %, from 0.00005 wt. % to 0.1 wt. %, from 0.0005 wt. % to 0.05 wt. %, from 0.00005 wt. % to 0.01 wt. %, from 0.00005 wt. % to 0.005 wt. %, from 0.00005 wt. % to 0.0001 wt. %, from 0.0001 wt. % to 0.5 wt. %, from 0.0001 wt. % to 0.1 wt. %, from 0.0001 wt. % to 0.05 wt. %, from 0.0001 wt. % to 0.01 wt. %, or from 0.0001 wt. % to 0.005 wt. %. In terms of upper limits, the acetonitrile product stream may comprise less than 0.5 wt. % methanol, e.g., less than 0.1 wt. %, less than 0.05 wt. %, less than 0.01 wt. %, less than 0.005 wt. %, or less than 0.0001 wt. %. In terms of lower limits, the acetonitrile product stream may comprise greater than 0 wt. % methanol, e.g., greater than 0.00005 wt. %, or greater than 0.0001 wt. %.

Purification of Acetonitrile Product Stream

As noted above, the acetonitrile product stream comprises relatively few impurities, e.g., methanol. In some embodiments, the acetonitrile product stream comprises a sufficiently high concentration of acetonitrile. As such, it may not be necessary to further purify the acetonitrile product stream. For example, in some case, an "ACN-grade" acetonitrile product is desired. In such cases, the successful formation of the acetonitrile product stream (with the accompanying acetonitrile purity) yields is a suitable and valuable commercial product. Other commercial grades that may be produced by the disclosed process include standard industrial grade, Laboratory Grade, ACS Grade, Chromatography Grade, LC Grade, and UHPLC Grade.

In some embodiments, a higher purity of acetonitrile may be desirable or necessary. As such, the acetonitrile product stream may be distilled, e.g., in a final distillation column, to yield a purified acetonitrile product stream. Various distillation columns are known to those of ordinary skill in the art, and any such column may be used as the final distillation in the present disclosure.

In some embodiments, the final distillation column operates at a pressure ranging from 100 mm Hg to 400 mm Hg, e.g., from 100 mm Hg to 375 mm Hg, from 100 mm Hg to 350 mm Hg, from 100 mm Hg to 325 mm Hg, from 100 mm Hg to 300 mm Hg, from 125 mm Hg to 400 mm Hg, from 125 mm Hg to 375 mm Hg, from 125 mm Hg to 350 mm Hg, from 125 mm Hg to 325 mm Hg, from 125 mm Hg to 300 mm Hg, from 150 mm Hg to 400 mm Hg, from 150 mm Hg to 375 mm Hg, from 150 mm Hg to 350 mm Hg, from 150 mm Hg to 325 mm Hg, from 150 mm Hg to 300 mm Hg, from 175 mm Hg to 400 mm Hg, from 175 mm Hg to 375 mm Hg, from 175 mm Hg to 350 mm Hg, from 175 mm Hg to 325 mm Hg, from 175 mm Hg to 300 mm Hg, from 200 mm Hg to 400 mm Hg, from 200 mm Hg to 375 mm Hg, from 200 mm Hg to 350 mm Hg, from 200 mm Hg to 325 mm Hg, or from 200 mm Hg to 300 mm Hg. In terms of lower limits, the final distillation column may operate at a pressure greater than 100 mm Hg, e.g., greater than 125 mm Hg, greater than 150 mm Hg, greater than 175 mm Hg, or greater than 200 mm Hg. In terms of upper limits, the final distillation column may operate at a pressure less than 400 mm Hg, e.g., less than 375 mm Hg, less than 350 mm Hg, less than 325 mm Hg, or less than 300 mm Hg.

In some embodiments, the final distillation column operates at a temperature ranging from 80° F. to 200° F., e.g., from 80° F. to 180° F., from 80° F. to 170° F., from 80° F. to 160° F., from 90° F. to 200° F., from 90° F. to 180° F., from 90° F. to 170° F., from 90° F. to 160° F., from 95° F. to 200° F., from 95° F. to 180° F., from 95° F. to 170° F., from 95° F. to 160° F., from 100° F. to 200° F., from 100° F. to 180° F., from 100° F. to 170° F., or from 100° F. to 160° F. In terms of lower limits, the final distillation column may operate a temperature greater than 80° F., e.g., greater than 90° F., greater than 95° F., or greater than 100° F. In terms of upper limits, the final distillation column may operate a temperature less than 200° F., e.g., less than 180° F., less than 170° F., or less than 160° F.

In some cases, the purification of the acetonitrile product stream comprises removing propionitrile therefrom. As noted above, the upstream operations, e.g., the removal of methanol and/or hydrogen cyanide, optionally in combination with the purification of the acetonitrile, has been found to yield a particularly high purity acetonitrile product.

In one embodiment, the purified acetonitrile product stream comprises acetonitrile in an amount ranging from 95 wt. % to 100 wt. %, e.g., from 95 wt. % to 99.999 wt. %, from 95 wt. % to 99.99 wt. %, from 97 wt. % to 100 wt. %, from 97 wt. % to 99.999 wt. %, from 97 wt. % to 99.99 wt. %, from 98 wt. % to 100 wt. %, from 98 wt. % to 99.999 wt. %, from 98 wt. % to 99.99 wt. %, from 99 wt. % to 100 wt. %, from 99 wt. % to 99.99 wt. %, from 99 wt. % to 99.9 wt. %, from 99.9 wt. % to 100 wt. %, from 99.9 wt. % to 99.999 wt. %, or from 99.9 wt. % to 99.99 wt. %. In terms of upper limits, the purified acetonitrile stream may comprise less than 100 wt. % acetonitrile, e.g., less than 99.999 wt. % or less than 99.99. In terms of lower limits, the purified acetonitrile stream may comprise greater than 95 wt. % acetonitrile, e.g., greater than 97 wt. %, greater than 98 wt. %, greater than 99 wt. %, greater than 99.9 wt. %, or greater than 99.99 wt. %.

In one embodiment, the purified acetonitrile product stream comprises low amounts (if any) propionitrile, e.g., in an amount ranging from 0 wt. % to 0.1 wt. %, e.g., from 0 wt. % to 0.05 wt. %, from 0 wt. % to 0.01 wt. %, from 0 wt. % to 0.005 wt. %, from 0 wt. % to 0.0001 wt. %, from 0.00005 wt. % to 0.1 wt. %, from 0.0005 wt. % to 0.05 wt. %, from 0.00005 wt. % to 0.01 wt. %, from 0.00005 wt. % to 0.005 wt. %, from 0.00005 wt. % to 0.0001 wt. %, from 0.0001 wt. % to 0.1 wt. %, from 0.0001 wt. % to 0.05 wt. %, from 0.0001 wt. % to 0.01 wt. %, or from 0.0001 wt. % to 0.005 wt. %. In terms of upper limits, the purified acetonitrile product stream may comprise less than 0.1 wt. % propionitrile, e.g., less than 0.05 wt. %, less than 0.01 wt. %, less than 0.005 wt. %, or less than 0.0001 wt. %. In terms of lower limits, the purified acetonitrile product stream may comprise greater than 0 wt. % propionitrile, e.g., greater than 0.00005 wt. %, or greater than 0.0001 wt. %.

In one embodiment, the purified acetonitrile product stream comprises low amounts (if any) oxazole, e.g., in an amount ranging from 0 wt. % to 0.1 wt. %, e.g., from 0 wt. % to 0.05 wt. %, from 0 wt. % to 0.01 wt. %, from 0 wt. % to 0.005 wt. %, from 0 wt. % to 0.0001 wt. %, from 0.00005 wt. % to 0.1 wt. %, from 0.0005 wt. % to 0.05 wt. %, from 0.00005 wt. % to 0.01 wt. %, from 0.00005 wt. % to 0.005 wt. %, from 0.00005 wt. % to 0.0001 wt. %, from 0.0001 wt. % to 0.1 wt. %, from 0.0001 wt. % to 0.05 wt. %, from 0.0001 wt. % to 0.01 wt. %, or from 0.0001 wt. % to 0.005 wt. %. In terms of upper limits, the purified acetonitrile product stream may comprise less than 0.1 wt. % oxazole, e.g., less than 0.05 wt. %, less than 0.01 wt. %, less than 0.005 wt. %, or less than 0.0001 wt. %. In terms of lower limits, the purified acetonitrile product stream may comprise greater than 0 wt. % oxazole, e.g., greater than 0.00005 wt. %, or greater than 0.0001 wt. %.

In one embodiment, the purified acetonitrile product stream comprises methanol in an amount ranging from 0 wt. % to 0.5 wt. %, e.g., from 0 wt. % to 0.1 wt. %, from 0 wt. % to 0.05 wt. %, from 0 wt. % to 0.01 wt. %, from 0 wt. % to 0.005 wt. %, from 0 wt. % to 0.0001 wt. %, from 0.00005 wt. % to 0.5 wt. %, from 0.00005 wt. % to 0.1 wt. %, from 0.0005 wt. % to 0.05 wt. %, from 0.00005 wt. % to 0.01 wt. %, from 0.00005 wt. % to 0.005 wt. %, from 0.00005 wt. % to 0.0001 wt. %, from 0.0001 wt. % to 0.5 wt. %, from 0.0001 wt. % to 0.1 wt. %, from 0.0001 wt. % to 0.05 wt. %, from 0.0001 wt. % to 0.01 wt. %, or from 0.0001 wt. % to 0.005 wt. %. In terms of upper limits, the purified acetonitrile product stream may comprise less than 0.5 wt. % methanol, e.g., less than 0.1 wt. %, less than 0.05 wt. %, less than 0.01 wt. %, less than 0.005 wt. %, or less than 0.0001 wt. %. In terms of lower limits, the purified acetonitrile product stream may comprise greater than 0 wt. % methanol, e.g., greater than 0.00005 wt. %, or greater than 0.0001 wt. %.

Separation Schemes

Beneficially, the disclosed system utilizes fewer columns than traditional systems, which provides the advantages of reducing complexity and capital cost, among others. In one embodiment, the separation scheme eliminates a column. In some cases the process comprises six distillation columns or fewer, e.g., five columns or fewer, four columns or fewer, three columns or fewer, or two columns or fewer. In some cases, the separation scheme comprises only six columns. In some cases, the separation scheme comprises only five columns. In some cases, the separation scheme comprises only four columns. In some cases, the separation scheme comprises only three columns.

In one embodiment, the separation scheme a purifies a feedstock stream comprising oxazole and propionitrile and produces an intermediate acetonitrile stream comprising less than 0.01 wt. % hydrogen cyanide, an acetonitrile product stream comprising less than 1 wt. % methanol, and a purified acetonitrile product stream comprising at least 99.5 wt. % acetonitrile.

In one embodiment, the separation scheme a purifies a feedstock stream further comprising allyl alcohol and produces an intermediate acetonitrile stream comprising less than 0.5 wt. % allyl alcohol, an acetonitrile product stream comprising less than 0.01 wt. % hydrogen cyanide, and a purified acetonitrile product stream comprises at least 99.8 wt. % acetonitrile.

In one embodiment, the separation scheme a purifies a feedstock stream further comprising oxazole, acetone, and propionitrile and produces an acetonitrile product stream comprising at least 98 wt. % acetonitrile and comprising less than 1 wt. % propionitrile.

In one embodiment, the separation scheme a purifies a feedstock stream comprising at least 80 wt. % water and produces an intermediate acetonitrile stream comprising less than 50 wt. % water, an acetonitrile product stream comprising at least 90 wt. % acetonitrile and less than 5 wt. % water, and a purified acetonitrile product stream comprising at least 99 wt. % acetonitrile and less than 0.5 wt. % water.

FIG. 1 shows an exemplary separation scheme 100. In the separation scheme 100, a feedstock stream 102 is fed to combined first distillation column 104, where it is distilled to yield the crude acetonitrile stream 106. The crude acetonitrile stream 106 is fed to a digester 108 to be treated with a caustic solution. The intermediate acetonitrile stream 110 is withdrawn from the digester 108. The intermediate acetonitrile stream 110 is then fed to the pressure swing distillation unit 112. A recycle stream 118 exits the pressure swing distillation unit 112 and is recycled to the first distillation column 104. The acetonitrile product stream 120 exits the pressure swing distillation unit 112 and is purified in final distillation column 122 to yield purified acetonitrile product stream 124.

Figure 2:
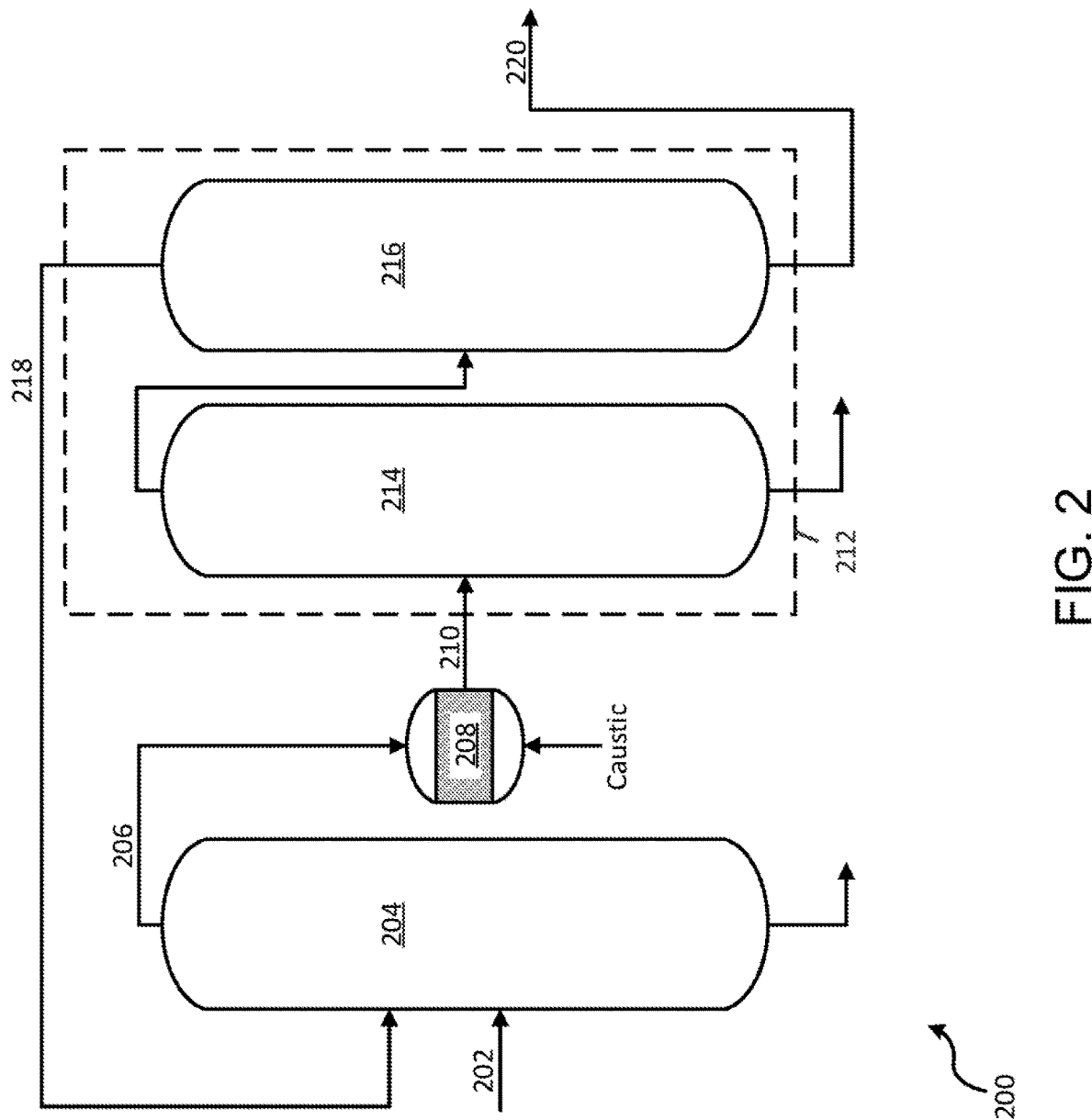
FIG. 2 illustrates a schematic of a process for recovering acetonitrile in accordance with embodiments of the disclosure.

FIG. 2 shows another exemplary separation scheme 200. In the separation scheme 200, feedstock stream 202 is fed to the first distillation column 204, where it is distilled to yield the crude acetonitrile stream 206. The crude acetonitrile stream 206 is fed to a digester 208 to be treated with a caustic solution. The intermediate acetonitrile stream 210 is withdrawn from the digester 208. The intermediate acetonitrile stream 210 is then fed to the pressure swing distillation unit 212, which comprises a low pressure distillation column 214 and a high pressure distillation column 216. A recycle stream 218 exits the high pressure distillation column 216 as an overhead and is recycled to the first distillation column 204. The acetonitrile product stream 220 exits high pressure distillation column 216 as a bottoms stream. In the separation scheme 200 of FIG. 2, the acetonitrile product stream 220 comprises a suitably high concentration of acetonitrile. Thus, in the separation scheme 200, there is no need to further purify the acetonitrile product stream 220.

Figure 3:
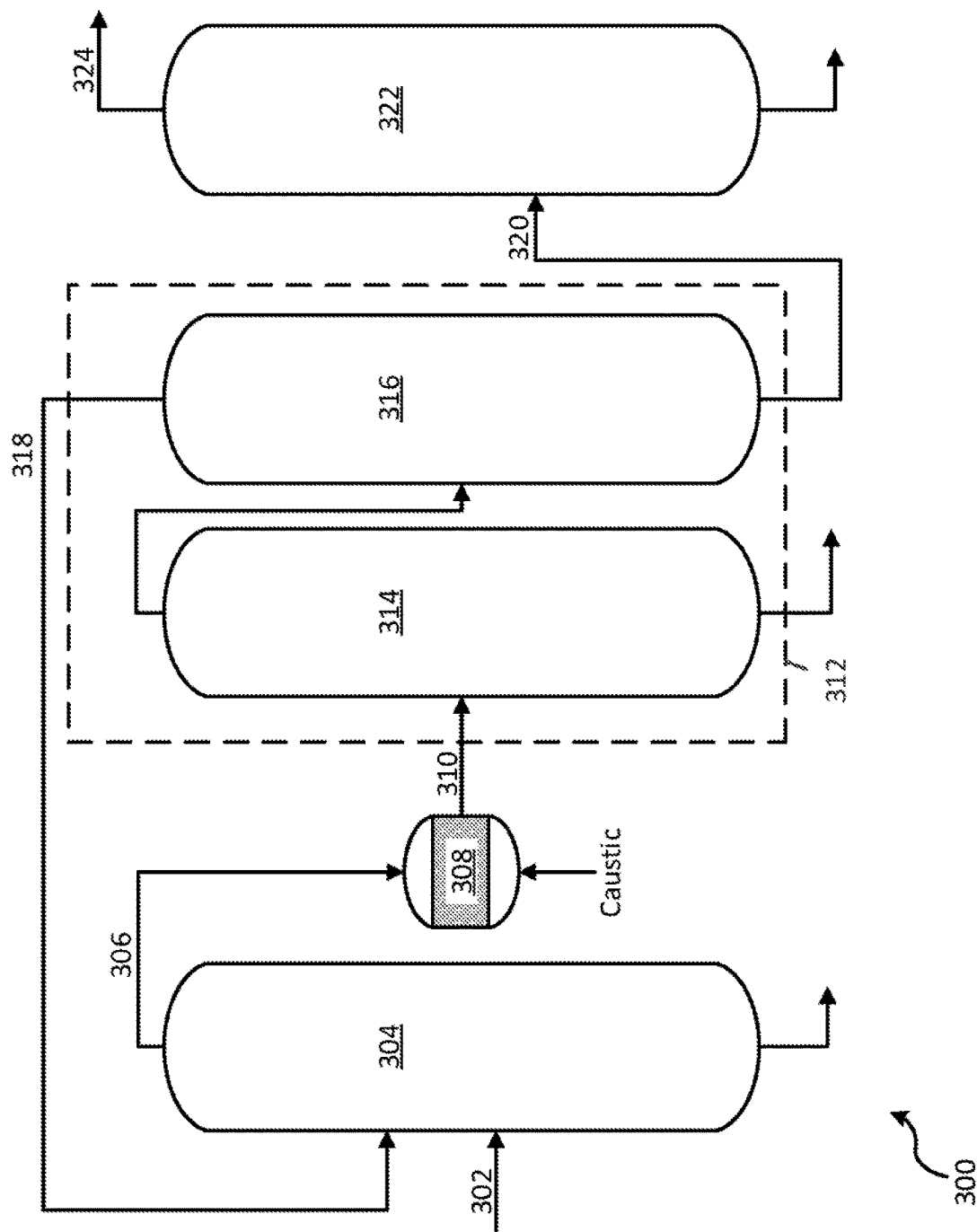
FIG. 3 illustrates a schematic of a process for recovering acetonitrile in accordance with embodiments of the disclosure.

FIG. 3 shows another exemplary separation scheme 300. In the separation scheme 300, feedstock stream 302 is fed to the first distillation column 304, where it is distilled to yield the crude acetonitrile stream 306. The crude acetonitrile stream 306 is fed to a digester 308 to be treated with a caustic solution. The intermediate acetonitrile stream 310 is withdrawn from the digester 308. The intermediate acetonitrile stream 310 is then fed to the pressure swing distillation unit 312, which comprises a low pressure distillation column 314 and a high pressure distillation column 316. A recycle stream 318 exits the high pressure distillation column 316 as an overhead and is recycled to the first distillation column 304. The acetonitrile product stream 320 exits high pressure distillation column 316 as a bottoms stream. Acetonitrile product stream 320 is purified in final distillation column 322 to yield purified acetonitrile product stream 324.

EXAMPLES

The present disclosure will be better understood in view of the following non-limiting example.

Example 1

A feedstock stream was prepared by combining three waste streams from an acrylonitrile production and purification process. The compositions of each waste stream, as well as the composition of the combined feedstock stream, are provided in Table 1, below.

The feedstock stream was distilled in first distillation column. The first distillation produced a bottoms stream, which primarily comprised water. The bottoms stream was discarded. The crude acetonitrile stream was removed from the first distillation column as a side cut. The crude acetonitrile stream was fed to a digester, into which aqueous sodium hydroxide was added to consume the hydrogen cyanide in the crude acetonitrile stream. An intermediate acetonitrile stream was then removed from the digester. The compositions of the bottoms stream of the first distillation column, the crude acetonitrile stream, and the intermediate acetonitrile stream are provided in Table 2, below.

The intermediate acetonitrile stream was then purified in a pressure swing distillation unit. In particular, the intermediate acetonitrile stream was distilled in a low pressure distillation column. The bottoms stream of the low pressure distillation column was discarded as waste. The overhead stream of the low pressure distillation column was condensed and distilled in a high pressure distillation column. A portion of the overhead of the high pressure distillation column was returned to the first distillation column as a recycle stream. The acetonitrile product stream was collected as the bottoms stream of the high pressure distillation column. The compositions of the bottoms stream of the low pressure distillation column, the condensed overhead of the low pressure distillation column, the recycle stream, and the acetonitrile product stream are provided in Table 3, below.

TABLE 1

Stream Compositions

| Component | Waste 1 (wt. %) | Waste 2 (wt. %) | Waste 3 (wt. %) | Feedstock (wt. %) |
|---|---|---|---|---|
| Acrylonitrile | 0.16 | 0.16 | 0.01 | 0.09 |
| Acetonitrile | 9.24 | 5.04 | 12.52 | 9.27 |
| $H_2O$ | 86.99 | 91.71 | 84.91 | 87.69 |
| HCN | 0.33 | 0.33 | 0.39 | 0.36 |
| MeOH | 1.50 | 1.00 | 0.15 | 0.70 |
| Allyl Alcohol | 0.04 | 0.04 | 0.11 | 0.07 |
| Oxazole | 0.26 | 0.26 | 0.55 | 0.39 |
| Acetone | 0.02 | 0.02 | 0.03 | 0.03 |
| Propionitrile | 0.04 | 0.04 | 0.05 | 0.04 |

TABLE 2

Stream Compositions - First Distillation

| Component | Col. 1 Bottoms (wt. %) | Crude ACN Stream (wt. %) | Intermed. ACN Stream (wt. %) |
|---|---|---|---|
| Acrylonitrile | 0.00 | 0.24 | 0.18 |
| Acetonitrile | 0.00 | 76.24 | 5605 |
| $H_2O$ | 98.4 | 18.79 | 33.73 |
| HCN | 0.00 | 0.11 | 0.00 |
| MeOH | 0.17 | 0.51 | 0.37 |
| Allyl Alcohol | 0.06 | 0.21 | 0.15 |
| Oxazole | 0.00 | 1.99 | 1.46 |
| Acetone | 0.00 | 0.03 | 0.02 |
| Propionitrile | 0.00 | 0.38 | 0.28 |

TABLE 3

Stream Composition - Pressure Swing Distillation

| Component | LP Col. Bottoms (wt. %) | LP Col. Overhead (wt. %) | Recycle Stream (wt. %) | ACN Product Stream (wt. %) |
|---|---|---|---|---|
| Acrylonitrile | 0.00 | 0.27 | 0.54 | 0.00 |
| Acetonitrile | 1.61 | 84.69 | 69.57 | 99.05 |
| $H_2O$ | 75.69 | 11.63 | 23.55 | 0.00 |
| HCN | 0.00 | 0.00 | 0.00 | 0.00 |
| MeOH | 0.01 | 0.57 | 1.15 | 0.00 |
| Allyl Alcohol | 0.31 | 0.07 | 0.01 | 0.13 |
| Oxazole | 0.01 | 2.23 | 4.51 | 0.00 |
| Acetone | 0.00 | 0.04 | 0.07 | 0.00 |
| Propionitrile | 0.00 | 0.43 | 0.16 | 0.69 |

Example 2

The same method as Example 1 was carried out. The acetonitrile was further purified by distilling in a final distillation column. The bottoms stream of the final distillation column was discarded as a waste stream. The overhead stream of the final distillation column was condensed as the purified acetonitrile product stream. The composition of the bottoms stream of the final distillation column and the purified acetonitrile product stream are provided in Table 4, below.

TABLE 4

Stream Compositions - Final Purification

| Component | Final Col. Bottoms (wt. %) | Pur. ACN Product Stream (wt. %) |
|---|---|---|
| Acrylonitrile | 0.00 | 0.00 |
| Acetonitrile | 0.00 | 99.98 |
| $H_2O$ | 0.00 | 0.00 |
| HCN | 0.00 | 0.00 |
| MeOH | 0.00 | 0.00 |
| Allyl Alcohol | 13.77 | 0.00 |
| Oxazole | 0.00 | 0.00 |
| Acetone | 0.00 | 0.00 |
| Propionitrile | 72.66 | 0.02 |

EMBODIMENTS

The following embodiments are contemplated. All combinations of features and embodiments are contemplated.

Embodiment 1

A process for recovering acetonitrile, comprising the steps of: distilling a feedstock stream comprising methanol and acetonitrile in a first distillation column to yield a crude acetonitrile stream, treating the crude acetonitrile stream to remove hydrogen cyanide and produce an intermediate acetonitrile stream comprising less than 1 wt. % hydrogen cyanide, purifying the intermediate acetonitrile stream in a pressure swing distillation system to produce an acetonitrile product stream and a recycle stream, and purifying the acetonitrile product stream to form a purified acetonitrile product stream comprising at least 98 wt. % acetonitrile.

Embodiment 2

An embodiment of embodiment 2, wherein the pressure swing distillation system comprises: a low pressure distillation column and a high pressure distillation column and wherein the high pressure distillation column yields an overhead stream and a bottoms stream.

Embodiment 3

The embodiment of embodiment 2, wherein the recycle stream is the overhead stream of the high pressure distillation column.

Embodiment 4

The embodiment of embodiments 2 or 3, wherein the acetonitrile product stream is the bottoms stream of the high pressure distillation column.

Embodiment 5

The embodiment of any of embodiments 1-4, wherein the acetonitrile product stream comprises less than 1 wt. % methanol, wherein the feedstock stream further comprises oxazole and propionitrile, wherein the intermediate acetonitrile stream comprises less than 0.01 wt. % hydrogen cyanide, and wherein the purified acetonitrile product stream comprises at least 99.5 wt. % acetonitrile.

Embodiment 6

The embodiment of any of embodiments 1-5, further comprising the step of recycling the recycle stream, which comprises methanol, to the first distillation column.

Embodiment 7

The embodiment of any of embodiments 1-6, wherein the recycle stream comprises at least 0.01 wt. % methanol.

Embodiment 8

The embodiment of any of embodiments 1-7, wherein the recycle stream comprises from 0.01 wt. % to 5 wt. % methanol.

Embodiment 9

The embodiment of any of embodiments 1-8, wherein the purifying of the acetonitrile product stream comprises distilling the acetonitrile product stream to yield the purified acetonitrile product stream.

Embodiment 10

The embodiment of any of embodiments 1-9, wherein the feedstock stream comprises at least 0.05 wt. % methanol.

Embodiment 11

The embodiment of any of embodiments 1-10, wherein the feedstock stream comprises less than 5 wt. % acetonitrile.

Embodiment 12

The embodiment of any of embodiments 1-11, wherein the feedstock stream further comprises propionitrile.

Embodiment 13

The embodiment of any of embodiments 1-12, wherein the treating comprises reacting the crude acetonitrile stream with a caustic solution to react out hydrogen cyanide.

Embodiment 14

The embodiment of any of embodiments 1-13, wherein the crude acetonitrile stream comprises from 0.1 wt. % to 5 wt. % hydrogen cyanide.

Embodiment 15

The embodiment of any of embodiments 1-14, wherein the intermediate acetonitrile stream comprises less than 0.05 wt. % hydrogen cyanide.

Embodiment 16

The embodiment of any of embodiments 1-15, wherein the feedstock stream comprises one or more waste streams from acrylonitrile production processes.

Embodiment 17

The embodiment of any of embodiments 2-16, wherein the low pressure distillation column operates at a pressure less than −5 psig.

Embodiment 18

The embodiment of any of embodiments 2-17, wherein the high pressure distillation column operates at a pressure greater than 10 psig.

Embodiment 19

The embodiment of any of embodiments 1-18, wherein the purified acetonitrile product stream comprises at least 99.9 wt. % of acetonitrile.

Embodiment 20

The embodiment of any of embodiments 1-19, wherein the purified acetonitrile product stream comprises less than 0.1 wt. % of propionitrile.

Embodiment 21

A process for recovering acetonitrile, comprising the steps of: distilling a feedstock stream comprising methanol and acetonitrile in a first distillation column to yield a crude acetonitrile stream, treating the crude acetonitrile stream to remove hydrogen cyanide and produce an intermediate acetonitrile stream comprising less than 1 wt. % hydrogen cyanide, and purifying the intermediate acetonitrile stream in a pressure swing distillation system to produce a recycle stream and an acetontrile product stream comprising at least 90 wt. % acetonitrile.

We claim:

1. A process for recovering acetonitrile, comprising the steps of:
    distilling a feedstock stream comprising methanol and acetonitrile present in an amount equal to or less than 10 wt % in a first distillation column to yield a crude acetonitrile stream comprising methanol,
    treating the crude acetonitrile stream to remove hydrogen cyanide and produce an intermediate acetonitrile stream comprising less than 1 wt. % hydrogen cyanide,
    purifying the intermediate acetonitrile stream in a pressure swing distillation system to produce an acetonitrile product stream and a recycle stream,
    purifying the acetonitrile product stream to form a purified acetonitrile product stream comprising at least 98 wt. % acetonitrile,
    wherein the first distillation column operates at a pressure greater than 0 psig.

2. The process of claim 1, wherein the pressure swing distillation system comprises:
    a low pressure distillation column and a high pressure distillation column and wherein the high pressure distillation column yields an overhead stream and a bottoms stream.

3. The process of claim 2, wherein the recycle stream is the overhead stream of the high pressure distillation column.

4. The process of claim 2, wherein the acetonitrile product stream is the bottoms stream of the high pressure distillation column.

5. The process of claim 1, wherein the acetonitrile product stream comprises less than 1 wt. % methanol, wherein the feedstock stream further comprises oxazole and propionitrile, wherein the intermediate acetonitrile stream comprises less than 0.01 wt. % hydrogen cyanide, and wherein the purified acetonitrile product stream comprises at least 99.5 wt. % acetonitrile.

6. The process of claim 1, further comprising the step of: recycling the recycle stream, which comprises methanol, to the first distillation column.

7. The process of claim 1, wherein the recycle stream comprises at least 0.01 wt. % methanol.

8. The process of claim 1, wherein the recycle stream comprises from 0.01 wt. % to 5 wt. % methanol.

9. The process of claim 1, wherein the purifying of the acetonitrile product stream comprises distilling the acetonitrile product stream to yield the purified acetonitrile product stream.

10. The process of claim 1, wherein the feedstock stream comprises at least 0.05 wt. % methanol.

11. The process of claim 1, wherein the feedstock stream comprises less than 5 wt. % acetonitrile.

12. The process of claim 1, wherein the feedstock stream further comprises propionitrile.

13. The process of claim 1, wherein the treating comprises reacting the crude acetonitrile stream with a caustic solution to react out hydrogen cyanide.

14. The process of claim 1, wherein the crude acetonitrile stream comprises from 0.1 wt. % to 5 wt. % hydrogen cyanide.

15. The process of claim 1, wherein the intermediate acetonitrile stream comprises less than 0.05 wt. % hydrogen cyanide.

16. The process of claim 1, wherein the feedstock stream comprises one or more waste streams from acrylonitrile production processes.

17. The process of claim 2, wherein the low pressure distillation column operates at a pressure less than −5 psig.

18. The process of claim 2, wherein the high pressure distillation column operates at a pressure greater than 10 psig.

19. The process of claim 1, wherein the purified acetonitrile product stream comprises at least 99.9 wt. % of acetonitrile.

20. The process of claim 1, wherein the purified acetonitrile product stream comprises less than 0.1 wt. % of propionitrile.

21. A process for recovering acetonitrile, comprising the steps of:
    distilling a feedstock stream comprising methanol and acetonitrile present in an amount equal to or less than 10 wt % in a first distillation column to yield a crude acetonitrile stream,
    treating the crude acetonitrile stream to remove hydrogen cyanide and produce an intermediate acetonitrile stream comprising less than 1 wt. % hydrogen cyanide, and
    purifying the intermediate acetonitrile stream in a pressure swing distillation system to produce a recycle stream and an acetontrile product stream comprising at least 90 wt. % acetonitrile,
    wherein the first distillation column operates at a pressure greater than 0 psig.

22. The process of claim 1, wherein the feedstock stream comprises from 0.01 wt. % to 1 wt. % methanol.

23. The process of claim 21, wherein the feedstock stream comprises from 0.01 wt. % to 1 wt. % methanol.

* * * * *